(12) United States Patent
Koenig et al.

(10) Patent No.: US 7,922,970 B2
(45) Date of Patent: Apr. 12, 2011

(54) USE OF SONICATION TO ELIMINATE PRIONS

(75) Inventors: David W. Koenig, Menasha, WI (US); Douglas R. Hoffman, Greenville, WI (US); Sara Carney, De Pere, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1043 days.

(21) Appl. No.: 11/695,834

(22) Filed: Apr. 3, 2007

(65) Prior Publication Data
US 2008/0248556 A1 Oct. 9, 2008

(51) Int. Cl.
*A61L 2/02* (2006.01)
*A61L 2/16* (2006.01)

(52) U.S. Cl. .......................................... 422/20; 422/128

(58) Field of Classification Search .................... 422/20, 422/128
See application file for complete search history.

(56) References Cited

U.S. PATENT DOCUMENTS

| | | | |
|---|---|---|---|
| 6,719,988 B2 | 4/2004 | Prusiner et al. | |
| 6,720,355 B2 | 4/2004 | Prusiner et al. | |
| 7,001,873 B2 | 2/2006 | McDonnell et al. | |
| 2002/0041859 A1 | 4/2002 | Prusiner et al. | |
| 2002/0192731 A1* | 12/2002 | H. Shih ........................ | 435/7.92 |
| 2003/0004312 A1 | 1/2003 | Prusiner et al. | |
| 2003/0073592 A1 | 4/2003 | McDonnell et al. | |
| 2003/0086820 A1 | 5/2003 | McDonnell et al. | |
| 2003/0148385 A1 | 8/2003 | Antloga et al. | |
| 2004/0052833 A1 | 3/2004 | Prusiner et al. | |
| 2004/0091474 A1 | 5/2004 | Raven et al. | |
| 2004/0106188 A1 | 6/2004 | Kritzler et al. | |
| 2004/0127558 A1 | 7/2004 | Prusiner et al. | |
| 2004/0127559 A1 | 7/2004 | Prusiner et al. | |
| 2006/0008494 A1 | 1/2006 | Prusiner | |
| 2007/0160493 A1 | 7/2007 | Ronholdt et al. | |

FOREIGN PATENT DOCUMENTS
WO 02062400 A1 8/2002

OTHER PUBLICATIONS

Cholchester, "The origin of bovine spongiform encephalopathy: the human prion disease hypothesis," The Lancet, 2005, p. 856-861, vol. 366.
Collins, et al., "Transmissible spongiform encephalopathies," The Lancet, 2004, p. 51-61, vol. 363.
Enserink, "After the crisis: More questions about prions," Science, 2005, p. 1756-1758, vol. 310.
Laemmli, "Cleavage of Structural Proteins during the Assembly of the Head of Bacteriophage T4," Nature, 1970, p. 680-685, vol. 227.
Langeveld, et al., "Enzymatic Degradation of Prion Protein in Brain Stem from Infected Cattle and Sheep," J. of Infectious Diseases, 2003, p. 1782-1789, vol. 188.
Lemmer, et al., "Decontamination of surgical instruments from prion proteins: in vitro studies on the detachment, destabilization and degradation of PrPSc bound to steel surfaces," J. of General Virology, 2004, p. 3805-3816, vol. 85.

(Continued)

*Primary Examiner* — Sean E Conley
(74) *Attorney, Agent, or Firm* — Armstrong Teasdale LLP (57) ABSTRACT

The present disclosure generally relates to methods for disinfecting surfaces. More particularly, the present disclosure relates to methods for destroying prion molecules using a combination of ultrasonic energy and enzyme treatment that is effective to denature and degrade prion proteins.

22 Claims, 3 Drawing Sheets

OTHER PUBLICATIONS

Peretz, et al., "Inactivation of Prions by Acidic Sodium Dodecyl Sulfate," Journal of Virology, Jan. 2006, p. 322-331, vol. 80, No. 1.

Piening, et al., "Breakage of PrP aggregates is essential for efficient autocatalytic propagation of misfolded prion protein," Biochemical and Biophysical Res. Com., 2005, p. 339-343, vol. 326.

Rutala, et al., "Creutzfeldt-Jakob disease: Recommendations for Disinfection and Sterilization," Healthcare Epidemiology, 2001, p. 1348-1356, vol. 32.

Silveria, et al., "The most infectious prion protein particles," Nature, 2005, p. 257-261, vol. 437.

Solassol, et al., "Detection of prion after decontamination procedures: comparative study of standard Western-blot, filter retention and scrapie-cell assay," J. of Hospital Infection, 2004, p. 156-161, vol. 57.

Suppattopone, et al., "Branched Polyamines Cure Prion-Infected Neuroblastoma Cells," J. of Virology, 2001, p. 3453-3461, vol. 75.

Wang, et al., "Enzymatic degradation of a prion-like protein, Sub35NM-His6," Enzyme and Microbial Technology, 2005, p. 758-765, vol. 36.

Watts, et al., "The expanding universe of prion diseases," PLoS Pathog, 2006, p. 0152-0163, vol. 2, No. 3., e26.

Riesner, et al., "Disruption of prion rods generates 10-nm spherical particles having high alpha-helical content and lacking scrapie infectivity," Journal of Virology, 1996, vol. 70, No. 3, p. 1714-1722.

International Search Report and Written Opinion from PCT/IB2008/051129, dated Aug. 11, 2008.

* cited by examiner

USE OF SONICATION TO ELIMINATE PRIONS

BACKGROUND OF DISCLOSURE

The present disclosure generally relates to methods for disinfecting surfaces, and in particular, methods for destroying prion molecules. More specifically, the methods use a combination of ultrasonic energy and enzyme treatment to denature and degrade the prions. The methods may be used to treat a surface, suspension, or solution contaminated with a prion or a surrogate thereof.

Many infectious agents such as bacteria, fungi, parasites, viruses, and viroids have well established methods of control that involve various forms of disinfection and sterilization (e.g. steam sterilization, dry sterilization, pasteurization, sterile filtration, treatment with ethylene oxide, glutaraldehyde, phenols or other disinfecting chemicals, radiation, etc.).

For several years, new and previously unknown pathogenic agents known as prions ("proteinaceous infectious particle") have appeared and have been reported in scientific publications. A number of relatively similar neurological diseases have been identified both in humans and animals, that appear to be attributable to prions. These diseases are generally referred to as transmissible spongiform encephalopathies (TSEs). TSEs include Creutzfeldt-Jakob disease (CJD), variant CJD (vCJD), Kuru, Gerstmann-Straussler-Scheinker disease (GSS), and fatal familial insomnia (FFI) in humans, bovine spongiform encephalopathy (BSE) in cattle (also know as "mad cow disease"), scrapie in sheep and goats, and chronic wasting disease in elk and deer. All of these diseases attack the neurological organs of the animal or animals that are susceptible to the particular disease. They are characterized by initially long incubation times followed by a short period of neurological symptoms, including dementia and loss of coordination, and eventually death.

The structure of prions has been the subject of intense investigation and different points of view have been expressed. Some scientists believe prions are extremely small viruses, while most experts now believe that prions are actually infectious proteins without a DNA or RNA core. More particularly, infectious prions are believed to be an abnormal form of a protein commonly found in the host (i.e., a PrP or "protease-resistant protein"). The PrP gene of mammals expresses a protein which can be the soluble, non-disease, cellular form $PrP^C$ or can be an insoluble disease form $PrP^{Sc}$. Many lines of evidence indicate that prion diseases result from the transformation of the normal cellular form into the abnormal $PrP^{Sc}$ form. There is no detectable difference in the amino acid sequence of the two forms. Rather, infectious prions are primarily distinguished from the cellular prion protein by their three-dimensional structure. Specifically, the cellular prion protein is predominately composed of the α-helix structure and is almost devoid of β-sheet. However $PrP^{Sc}$ has an altered conformational form, in particular having a high level of β-sheet conformation and a large number of intra-molecular disulfide bonds, which makes $PrP^{Sc}$ highly resistant to elimination under all but extreme conditions.

The pathogenic mechanism for prion diseases is proposed to involve a change in the normal host encoded protein. The protein undergoes a conformational change to the abnormal $PrP^{Sc}$ form, which has the ability of self-propagation. The exact cause of this change is, at present, unknown. The abnormal form of the protein is not broken down effectively in the body and its accumulation in certain tissues (in particular neural tissue) eventually causes tissue damage, such as cell death. Once significant neural tissue damage has occurred, the clinical signs are observed.

Although prion diseases have not generally been considered to be highly contagious, they can be transmitted within a species and, under certain conditions, from one species to another. It has recently been shown that prion diseases may be transmitted via high risk tissues, including the brain, spinal cord, cerebral spinal fluids, and the eye. Iatrogenic transmission has also been reported, including transmission via dura mater grafting, corneal transplants, pericardial homografts, and human gonadotropin and human growth hormone contamination. Transmission via medical devices has also been reported. For instance, after a surgical procedure on a prion infected patient, prion containing residue may remain on the surgical instruments, particularly neurosurgical and opthalmological instruments, depth electrodes, and other devices used during surgeries in close proximity to the central nervous system. There are also concerns that groups at risk may also include veterinarians, abattoir workers, and butchers in contact with cows or beef, primarily in Europe.

There is currently much speculation about the efficacy of conventional decontamination and sterilization methods for destruction of prions. As noted above, prions are notoriously very hardy and demonstrate resistance to routine methods of decontamination and sterilization. Conventional hospital disinfectants including ethylene oxide, propriolactone, hydrogen peroxide, iodophors, peractic acid, chaotropes and phenolics have little effect on prion infectivity. In addition, infectious prions are resistant to UV irradiation, aldehyde fixation, boiling, standard gravity autoclaving at 121° C., and detergent solubilization. Although prions can be inactivated by relatively high temperatures over very long periods of time, the temperature ranges and time periods generally used to kill bacteria and inactivate the viruses are insufficient to inactivate prions. Furthermore, because prions do not contain nucleic acids, traditional sterilization methods that act by destroying or disrupting DNA or RNA are also ineffective against prions.

Some recommended methods for inactivating prions include incineration, prolonged steam autoclaving, and sodium hydroxide and sodium hypochlorite treatments at high concentrations. However, these aggressive treatments are often incompatible with expensive medical and surgical devices, particularly flexible endoscopes and other devices with plastic, brass, aluminum, or non-metallic parts. Many such devices are damaged by exposure to high temperatures, while chemical treatments, such as strong alkali, are damaging to medical device materials or surfaces in general.

Because of these limitations, prion decontamination of surgical or dental equipment is often performed only after operations on patients suspected to have CJD. Typically, standard protocols used to sterilize instruments following operations on all other patients, such as routine autoclaving, do not inactivate prions. Because of the difficulties involved in decontamination, it has also been proposed as preferable that surgical instruments used in brain surgery should be used only once. This, however, implies a disposal risk in addition to being expensive and for some instruments impractical. The extreme conditions required to destroy prions also make the cleaning of surfaces difficult, such as in a surgical or meat processing setting. Additionally, these conditions require special considerations and safety protocols be undertaken by personnel working with the instruments being cleaned.

There is thus a clear need for a cleaning process that is effective at eliminating prions, but does not use harsh conditions traditionally required for prion destruction or inactivation. Such a method could advantageously be used for routine prion decontamination of all surgical instruments to prevent cases of iatrogenic transmission of TSEs, and for decontamination of other prion contaminated surfaces, suspensions, and solutions.

SUMMARY OF THE DISCLOSURE

The present disclosure generally relates to methods for disinfecting surfaces. More particularly, the present disclosure relates to methods for destroying prion molecules. Specifically, the methods use a combination of ultrasonic energy and enzyme treatment to denature and degrade the prions. The methods may be used to treat a surface, suspension, or solution contaminated with a prion or a surrogate thereof.

In one aspect, the present disclosure is directed to a method of disinfecting a surface contaminated with a prion protein or a surrogate thereof. The method comprises treating the surface with a means for denaturing the prion protein, the denaturing means being selected from the group consisting of ultrasonic energy, electric fields, magnetic fields, and combinations thereof; and treating the surface with a degradation composition comprising one or more enzymes effective to cleave the prion protein into non-infective fragments; wherein the degradation composition is substantially free of a surfactant.

In another aspect, the present disclosure is directed to a method of disinfecting a surface contaminated with a prion protein or a surrogate thereof. The method comprises treating the surface with a means for denaturing the prion protein, the denaturing means being selected from the group consisting of ultrasonic energy, electric fields, magnetic fields, and combinations thereof; and treating the surface with a degradation composition comprising one or more enzymes effective to cleave the prion protein into non-infective fragments; wherein the degradation composition has a pH of from about 6 to about 8.

In yet another aspect, the present disclosure is directed to a method of disinfecting a surface. The method comprises treating the surface with a denaturing means selected from the group consisting of ultrasonic energy, electric fields, magnetic fields, and combinations thereof; and treating the surface with a degradation composition comprising one or more enzymes selected from the group consisting of proteases, proteolytic enzymes, and combinations thereof; wherein the degradation composition has a pH of from about 6 to about 8.

In still another aspect, the present disclosure is directed to a method of disinfecting a surface. The method comprises treating the surface with a denaturing means selected from the group consisting of ultrasonic energy, electric fields, magnetic fields, and combinations thereof; and treating the surface with a degradation composition comprising one or more enzymes selected from the group consisting of proteases, proteolytic enzymes, and combinations thereof; wherein the degradation composition is substantially free of a surfactant.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

The present disclosure generally relates to methods for destroying prions or rendering prions non-infective. In particular, the methods may be used to disinfect surfaces, solutions, or suspensions that are contaminated with infective prions.

As used herein, the terms "prion," "prion protein," "infectious protein," "PrP$^{Sc}$ protein" and the like are used interchangeably to refer to the infectious PrP$^{Sc}$ form of a PrP protein. The term "prion surrogate" as used herein refers to proteins having a resistance to proteases similar to infective prions due to the presence of β-folding. One type of prion surrogate protein (PSP) is available from BioResource International, Inc. (Chapel Hill, N.C.), catalog number PSP-001.

As discussed above, the PrP$^{Sc}$ prion form is highly resistant to destruction under all but extreme conditions, such as very high temperatures, extreme pH, or harsh chemicals. Furthermore, PrP$^{Sc}$ protein is characteristically resistant to attack by enzymes including proteolytic enzymes. Without wishing to be bound by theory, it is believed that the resistance of PrP$^{Sc}$ protein to attack by enzymes and other common disinfection methods is a result of the altered folded conformation of infectious prions. In particular, PrP$^{Sc}$ has a high level of β-sheet conformation, relative to the number of α-helical structures, and a high number of intra-molecular disulfide bonds, which make PrP$^{Sc}$ highly resistant to elimination.

Many proteins are prone to lose their natural three dimensional folding pattern ("secondary and tertiary structure") and to become "denatured". The denaturation includes breakdown of the intramolecular interaction, especially hydrogen and disulfide bonds, and thus the loss of the secondary structure which virtually all native proteins have in at least parts of the molecule, and which generally is decisively responsible for the activity of the protein. PrP$^{Sc}$ protein, on the other hand, is highly resistant to unfolding and thus resistant to attack by proteolytic enzymes. The present disclosure addresses this problem by providing a means for prion destruction, by denaturing or unfolding the prion protein sufficiently for an enzyme to gain access to and cleave PrP$^{Sc}$ protein to sizes that are non-infective and safe (e.g., having a molecular weight of less than 27 kDa).

Specifically, the methods of the present disclosure use a combination of chemical and physical agents to unfold (i.e., denature) the prion molecule, and cleave the unfolded prion into non-infective fragments. More specifically, the methods use a combination of ultrasonic energy and enzyme treatment to denature and degrade the prions or prion surrogates.

Thus, according to one aspect of the present disclosure, a method of disinfecting a surface (e.g., a surgical instrument), such as a surface contaminated with a prion protein or a surrogate thereof, is disclosed. Although discussed primarily herein in terms of prion-contaminated surfaces, it should be recognized that the methods described herein may also be used to disinfect prion contaminated suspensions, solutions, and the like. Additionally, the methods described herein advantageously have application as general methods for disinfection of medical, surgical, and food processing equipment. For instance, while discussed primarily in connection with eliminating prions, the methods may also be effective at eliminating other infective microorganisms, and may be used as a routine disinfection process for surfaces such as medical or surgical devices or instruments, food processing equipment (e.g., meat processing equipment), and the like.

Specifically, the methods comprise treating the surface to be disinfected with a means for denaturing a prion protein and with a degradation composition comprising one or more enzyme effective to cleave a prion protein into non-infective fragments. The surface may be treated with the denaturing means and degradation composition simultaneously, or alternately, may be treated first with the denaturing means and subsequently treated with the degradation composition.

Advantageously, it has been discovered that the application of energy, such as ultrasonic energy, magnetic fields, electric fields, and the like, to a surface contaminated with prions is effective to denature the prions. In this regard, it should be understood that complete denaturation of the prions is not necessary for the methods of the present disclosure to be effective. Rather, the prions need only be denatured to an extent sufficient to allow the enzymes in the degradation composition access to the prion protein, so that the enzymes can cleave the prion into non-infective fragments.

In a particularly preferred embodiment, denaturation is achieved by use of ultrasonic energy. More specifically, the surface is subjected to sound waves in the ultrasonic range during the treatment. Sonication utilizes high frequency sound waves to disrupt a liquid solution. Without intending to be bound by theory, it is believed that this disruption causes cavitation where microscopic bubbles form and collapse, thereby generating significant amounts of energy that loosen prion particles attached to the surface being disinfected. Sonication also acts to break intramolecular bonds and to denature the prions.

Preferably, the sonication is conducted at a frequency of at least about 20 kHz, more preferably, at a frequency of from about 20 kHz to about 30 kHz, and still more preferably at a frequency of about 24 kHz. Preferably, the sonication is performed at a power of from about 1 watt to about 20 watts, more preferably at about 7 watts to about 10 watts, and still more preferably at about 8 watts or about 9 watts, and produces from about 30 to about 144,000 joules of energy, and more preferably about 5000 to about 36,000 joules of energy.

While the amount of time sonication is performed may vary depending on the amount of energy produced, preferably sonication is performed for from about 0.5 minutes to about 120 minutes, and more preferably for from about 20 minutes to about 60 minutes. In general, the amount of time sonication needs to be performed will decrease as the amount of applied energy increases. It is also to be understood that sonication can be continuous sonication for the given time period or it can be discontinuous sonication for the given time period. Discontinuous sonication is also referred to as on/off or off/on pulsing. Numerous suitable sonication devices are commercially available, such as, for example, Vibra Cell model VC 505, available from Sonics, Inc. (Newton, Conn.), among others.

In addition to sonication, prion denaturation may be induced or aided by other forms of energy input, such as radiation in the radiofrequency spectrum, electromechanical radiation or energetic vibration from mechanical means such as magnetic or vortex stirring, electron beam irradiation, laser, electrolysis, or other forms of acoustic energy. Particularly preferred denaturation means are selected from the group consisting of ultrasonic energy, electric fields, magnetic fields, and combinations thereof.

Advantageously, the denaturation step of the methods described herein occurs in the absence of harsh conditions, such as high or low pH, high temperatures, or harsh detergents or chemicals that may act to corrode or otherwise damage the surface or device being treated. For instance, the surface being treated (such as a surgical instrument contaminated with an infectious prion) may be suspended in water, detergent solutions, and/or solvent solutions, or other non-corrosive and mild agents during sonication. Preferably, the denaturation occurs at a pH of from about 5 to about 9, more preferably at about 6 to about 8, and still more preferably at about 7.0, and a temperature of from about 10° C. to about 95° C., more typically from about 20° C. to about 50° C., and still more typically at about 30° C.

As noted above, the surface may first be treated with the denaturing means and subsequently treated with the degradation composition or, alternately, the surface undergoing treatment may be subjected to the denaturation means and degradation composition simultaneously. For instance, a device or surface being treated may be suspended in the degradation composition prior to or during denaturation.

As noted above, the degradation composition comprises one or more enzyme that is effective to cleave a prion protein into non-infective fragments. Any enzyme having such activity may be used. Preferably, the enzyme is selected from the group consisting of proteases, other proteolytic enzymes, and combinations thereof. Examples of suitable proteases include serine proteases, cysteine proteases, metalloproteases, threonine proteases, aspartic acid proteases, and glutamic acid proteases. Specific examples of serine proteases include Subtilisin serine proteases such as proteinase K and PROPERASE® enzyme (Genecor International, Inc.); and chymotrypsin-like serine proteases such as chymotrypsin, trypsin, and elastase. Specific examples of cysteine proteases include papain, cathepsins, caspases, and calpain proteases. Examples of other suitable proteases include keritinases and collagenases. In one embodiment, the enzymes may preferable be thermostable, such as thermostable metalloproteases. Optionally, the protease may be a cold-tolerant protease, such as the serine alkaline protease isolated from a *Shewanella* sp.

The degradation composition may comprise from about 0.05 µg/mL to about 150 µg/mL, and preferably from about 0.1 µg/mL to about 80 µg/mL of the protease and/or other proteolytic enzyme. In other embodiments, the degradation composition may comprise from about 0.01% (w/w) to about 10% (w/w), preferably from about 1% (w/w) to about 5% (w/w), and preferably from about 3% (w/w) to about 5% (w/w) protease and/or other proteolytic enzyme.

In one preferred embodiment, the degradation composition is substantially free of denaturation agents. By "substantially free of denaturation agents" it is meant that no additional denaturation agents are affirmatively added to the degradation composition. In particular, certain surfactants are known to denature proteins. Such surfactants may, however, also damage sensitive medical instruments or other types of equipment that are being disinfected, or in certain instances, may act to denature the protease or other proteolytic enzymes present in the degradation composition, thus rendering the enzymes ineffective. Thus, in one embodiment, the degradation composition is substantially free of surfactants, meaning no surfactant is affirmatively added to the degradation composition.

Alternately, in certain instances, it may be advantageous to include in the degradation composition an agent that promotes denaturation, to further assist in unfolding prions. In instances where an additional denaturing agent is included in the degradation composition, it is not necessary that the additional denaturing agent be capable of completely unfolding the prion molecule, but instead it may act to supplement the unfolding achieved by treatment with the denaturing means, described above. Thus, in an alternate embodiment, the degradation composition may comprise agents capable of denaturing prions. Examples of denaturing agents that may be included in the degradation composition include, for example, surfactants, organic solvents, inorganic salts, chaotropic agents, and combinations thereof.

Suitable chaotropic agents include, for example, urea, guanidine hydrochloride, and the like.

Suitable organic solvents include those which tend to denature, dissolve, or swell proteins. Generally the products are not completely unfolded and possess an ordered conformation which differs from the native state. Solvents which favor helical conformations (i.e. unfolding) are exemplified by N-dimethylformamide, formamide, m-cresol, dioxan, $CHCl_3$, pyridine, dichlorethylene, and 2-chloroethanol. This group also includes solvents which have a weak tendency to form hydrogen bonds such as the alcohols, ethanol, n-propanol, methanol (especially in mixture with 0.01% HCl). Also, solvents which tend to disorganize the structure e.g. dimethylsulphoxide (DMSO) at high concentrations, dichloroacetic acid and trifluoroacetic acid, and other electrophilic solvents can be used.

Suitable inorganic salts include those that can induce conformational transitions in proteins. For example LiBr, $CaCl_2$, KSCN, NaI, NaBr, sodium azide are strong denaturants. Although these salts do not necessarily lead to completely unfolded protein, the residual ordered structure may be disrupted by energy input e.g. increasing temperature. Anions such as $CNS^->I^->Br^->NO_3^->Cl^->CH_3COO^->SO_4^-$ exhibit similar behaviour as do guanidinium salts and tetraalkyl ammonium salts. However $(GuH)_2SO_4$ has been observed to protect certain proteins against denaturation.

In one specific embodiment, the degradation composition comprises a surfactant. The surfactant may be an anionic surfactant, cationic surfactant, non-ionic surfactant, zwitterionic surfactant, or some combination thereof. Preferably, the surfactant is an anionic surfactant.

Examples of suitable anionic surfactants include sodium dodecyl sulfate (SDS), dodecyl benzene sulfonate, nonyl phenol ethoxylate, alpha olefin sulfonate, ammonium laureth sulfate, ammonium laureth ether sulfate, ammonium octyl\decyl ether sulfate, ammonium stearate, sodium laureth sulfate, sodium lauryl sulfate, octyl sulfate, sulfonate, sulfosuccinimate, tridecyl ether sulfate, triethanolamine lauryl sulfate, and combinations thereof. Preferably, the anionic surfactant is sodium dodecyl sulfate.

Examples of suitable non-ionic surfactants include alkoxylates, ethoxylates, phthalamates, triglycerides, amides, esters, and combinations thereof.

Examples of suitable cationic surfactants include polyquaterium 1, ester quaternary compounds, quaternary ammonium chloride compounds, quaternary ammonium methyl sulfate compounds, and combinations thereof.

Examples of suitable zwitterionic surfactants include cocoamidopropyl betaine, laurylamidopropyl betaine, lauryl dimethyl amine oxide, cocoamidopropyl dimethyl amine oxide, and combinations thereof.

The degradation composition may comprise from about 0.1% (w/w) to about 20% (w/w) of a surfactant, and preferably comprises from about 5% (w/w) to about 15% (w/w) of a surfactant.

It will be recognized that proteases are themselves enzymes. It has been discovered, however, that when the surface undergoing treatment is simultaneously subjected to the denaturation means and degradation composition of the present disclosure, or if the degradation composition comprises denaturation agents, such as those described herein, the proteolytic enzymes present in the degradation composition are not themselves inactivated by the denaturation means or additional denaturation agents. This is illustrated by the results shown in Example 3. Without wishing to be bound to any particular theory, it is believed the proteolytic enzymes present in the degradation composition may be stabilized when they are associated with the prion being degraded.

Even so, in certain embodiments, it may be desirable to include in the degradation composition stabilizing agents to prevent to the enzymes present in the degradation composition from being denatured and inactiveated by the denaturation means or by additional denaturation agents that may be present in the degradation composition. Examples of suitable stabilizing agents include, for example, divalent metals such as calcium and magnesium, boron, dioxane, acetonitrile, dimethylformamide, pyridine, glycerol, ethylene glycol, propylene glycol, sucrose, citrate, acetate, phosphates, and the like, and combinations thereof.

Generally, the degradation composition also comprises water. The composition can additionally include other ingredients such as additional surfactants, preservatives, chelating agents, pH adjusting agents, fragrances, enzyme and protease stabilizers, emulsifiers, and combinations thereof. In one particularly embodiment, the degradation composition comprises from about 5% to about 15% (w/w) of a surfactant (e.g., nonyl phenol ethoxylate), from about 15% to about 30% (w/w) of a protease stabilizer (e.g., propylene glycol), from about 5% to about 10% (w/w) of an emulsifier (e.g., triethanolamine), from about 2% to about 5% (w/w) of an enzyme stabilizer (e.g., boron), from about 0% to about 3% (w/w) of a preservative (e.g., an antimicrobial agent), from about 3% to about 5% (w/w) of a protease, from about 0% to about 0.1% (w/w) of a fragrance oil, and from about 7% to about 7.5% of a pH adjuster (e.g., acetic acid), with the remainder comprising water.

Examples of additional emulsifiers that may be included in the degradation composition include triethanolamine, alginates, tartrates, carrageenan, sorbitol, polysorbates, and the like, and combinations thereof.

It is generally preferable for the pH of the degradation composition to be at or around neutral. As discussed above, while compositions with high or low pH may be effective at eliminating prions, such compositions may also corrode, make brittle, or otherwise damage non-metallic substrates and medical, surgical, or other devices being cleaned. The damaging effects of strongly alkaline or acidic disinfecting compositions are especially seen when such compositions are used repeatedly over extended periods of time.

Advantageously, the present disclosure addresses these concerns, by providing a degradation composition that is at or around a neutral pH. Thus, the degradation composition of the present disclosure preferably has a pH of from about 5 to about 9, more preferably of from about 6 to about 8, and still more preferably about 7.0.

Typically, the temperature of the degradation composition is from about 10° C. to about 95° C., more typically is from about 20° C. to about 50° C., and still more typically is about 30° C.

The amount of time the surface is treated with the degradation composition may vary, but is typically from about 0.5 minutes to about 120 minutes, and more preferably is from about 20 to about 60 minutes.

The methods described herein have application as general methods for disinfecting surfaces, as well as for specifically disinfecting prion contaminated surfaces, suspensions, solutions, and the like. As used herein, the term "surface" is meant to include surfaces in general, including metallic and non-metallic surfaces, as well as devices such as medical, surgical, and/or dental devices, instruments or equipment. The term "surface" may also include food processing surfaces and equipment (such as meat processing equipment), as well as the meat being processed (e.g., meat from domestic animals and wild game), and the like.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

Stability of Prion Surrogate Protein

In this example, the suitability of prion surrogate protein (PSP) as a prion model was evaluated. In particular, PSP has been reported to replicate the structural characteristics of infective mammalian prions. This example examined the stability of PSP under conditions known to be suitable for sodium dodecyl sulfate (SDS) denaturation of infective mammalian prions.

50 µg/ml PSP (available from BioResource International, Inc., Chapel Hill, N.C., catalog number PSP-001) was treated with either 0% (w/v), 1% (w/v), 4% (w/v), or 8% (w/v) SDS for 20 minutes. The sample containing PSP alone (0% (w/v) SDS) was suspended in a phosphate buffered saline (PBS) solution. The PSP samples were then digested with proteinase K using the following procedure:

10 µg of each sample was digested with proteinase K at a concentration of 100:1 (PSP to proteinase K). The proteinase K digestions were conducted for 30 minutes at 37° C. The digestions were halted by the addition of 8 µL of 0.5 M phenylmethylsulfonyl fluoride (PMSF) heated to 37° C. Samples were visualized using Western blotting.

Western blots were conducted following the protocol outlined in product literature included with the Immun-Star® chemiluminescent blotting kit (available from Bio-Rad (Hercules, Calif.)). Unless otherwise indicated, reagents used for Western blot analysis were those provided in the Immun-Star® chemiluminescent blotting kit.

To begin, samples were electrophoresed using sodium dodecyl sulfate polyacrylamide gel electrophoresis (SDS-PAGE). 5 µg of each sample was diluted 1:1 with 2× SDS sample buffer (Novex Tris-Glycine SDS Sample Buffer (2×), available from Invitrogen, Carlsbad, Calif.) and boiled for 12 minutes at 100° C. Samples were loaded onto 4-12% Bis-Tris acrylamide gels (available from Invitrogen, Carlsbad, Calif.) and electrophoresed at 30 mA until the dye front reached the bottom of the gel. Gels were removed from their encasing plates and fixed in 50% methanol-10% acetic acid-40% water for 15 minutes, stained in Coomassie Blue stain for 30 minutes, and destained in 45% methanol-10% acetic acid-45% water until the protein bands became distinct.

Following SDS-PAGE, the proteins were transferred onto nitrocellulose membranes overnight. Membranes were blocked in 5% non-fat milk plus tris-buffered saline/0.1% Tween 20, and incubated with primary antibody (Bio-Rad International, Inc. (Hercules, Calif.)) at a 1:3000 ratio overnight with gentle shaking. The following day, membranes were washed 6 times for 10 minutes per wash with Tris-buffered saline/0.1% Tween 20, changing the wash solution between washes. Membranes were incubated in secondary antibody (Bio-Rad International, Inc. (Hercules, Calif.)) at a 1:20,000 ratio for 60 minutes, and again washed 6 times for 10 minutes per wash as described above. Membranes were incubated with the chemiluminescent substrate provided in the Immun-Star® kit (Bio-Rad International, Inc.) for 5 minutes, and imaged using software and equipment from Alpha Innotech (San Leandro, Calif.). The results are shown in FIG. 1.

Figure 1:
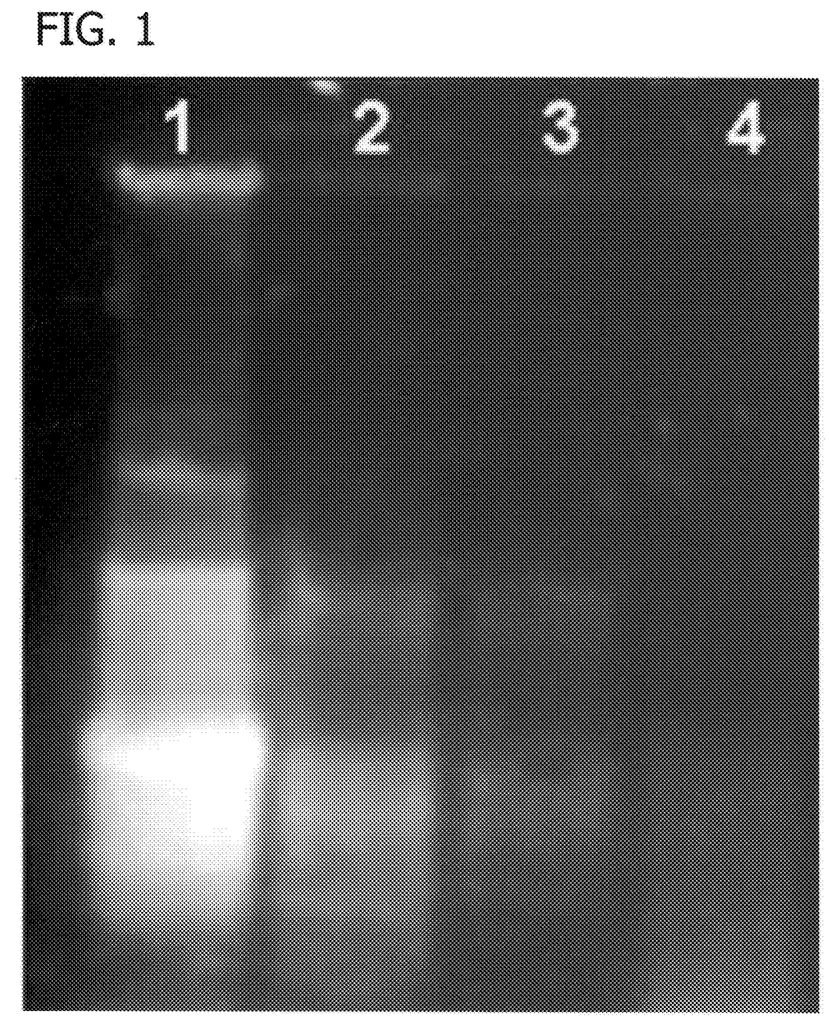
FIG. 1 is a Western blot of prion surrogate protein (PSP) digested with proteinase K following pre-treatment with either 0% (w/v) (Lane 1), 1% (w/v) (Lane 2), 4% (w/v) (Lane 3), or 8% (w/v) (Lane 4) sodium dodecyl sulfate, as described in Example 1.

As can be seen from FIG. 1, a greater quantity of PSP remained in the sample pre-treated with 1% (w/v) SDS (Lane 2) than in the sample pre-treated with 4% (w/v) SDS (Lane 3), while no PSP remained in the sample treated with 8% (w/v) SDS (Lane 4). Results for the sample comprising PSP alone (0% (w/v) SDS) is shown in Lane 1. Since the use of SDS has been reported as a reliable method for denaturing infective prions at a minimum concentration of 4% (w/v), these results suggest that PSP reacts similarly to infective prions under conditions of SDS denaturation.

Example 2

Effect of Sonication on Prion Surrogate Protein Stability

In this example, prion surrogate protein (PSP) was used to demonstrate the efficacy of ultrasonic energy at inducing prion denaturation. In particular, the efficacy of sequentially treating PSP with ultrasonic energy followed by treatment with proteinase K to destroy prions was evaluated.

50 µg of PSP (available from BioResource International, Inc., Chapel Hill, N.C., catalog number PSP-001) was added to two sterile polystyrene test tubes (5 mL) and sonicated using a Vibra Cell model VC 505 from Sonics, Inc (Newton, Conn.) at 36% amplitude for 60 minutes (approximately 9 watts continuous, 35,940 joules of energy). The PSP samples were then either digested with proteinase K, or mixed with a sufficient amount of phosphate buffered saline (PBS) to maintain the same volume as the proteinase K treated samples following exposure to ultrasonics. The proteinase K digestions were performed using the following procedure:

10 µg of sonicated PSP was digested with proteinase K at a concentration of 100:1 (PSP to proteinase K). The proteinase K digestions were conducted for 30 minutes at 37° C. The digestions were halted by the addition of 8 µL of 0.5 M phenylmethylsulfonyl fluoride (PMSF) heated to 37° C. Samples were visualized using Western blotting, as described in Example 1.

Figure 2:
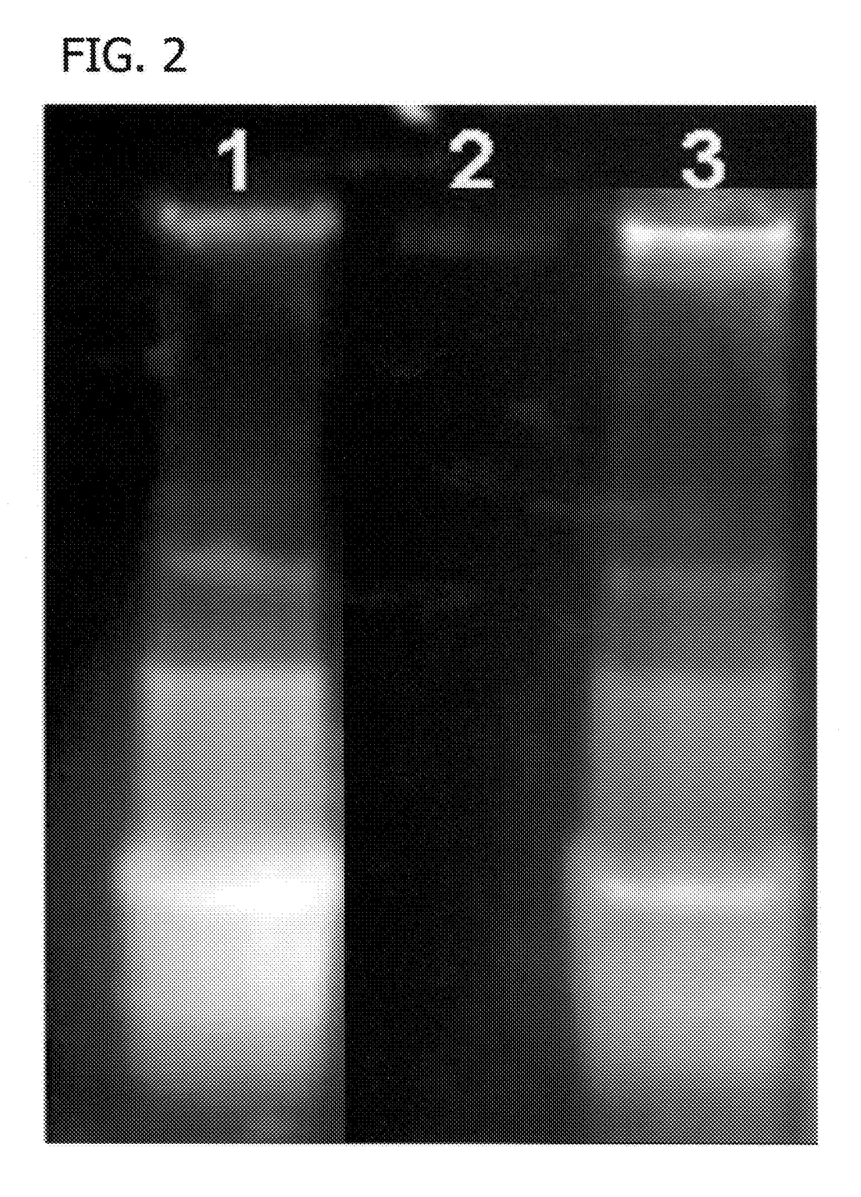
FIG. 2 is a Western blot of either PSP alone (no sonication, no proteinase K digestion) (Lane 1), PSP sonicated followed by digestion with proteinase K (Lane 2), or PSP sonicated but not digested with proteinase K (Lane 3), as described in Example 2.

The results are shown in FIG. 2. Lane 1 shows the results for PSP alone (no sonication pre-treatment, and no proteinase K digestion), Lane 2 shows the results for PSP pretreated with ultrasonics for 1 hour followed by digestion with proteinase K, and Lane 3 shows results for PSP pretreated with ultrasonics for 1 hour, followed by the addition of PBS. As can be seen from these results, no PSP was detected in Lane 2 (sonicated+ proteinase K digestion), thus indicating that exposing PSP to sonication (at ~9 watts continuous with 35,940 joules of energy) denatured the PSP significantly enough to make the PSP sensitive to proteinase K digestion.

Example 3

Effect of Sonication on Prion Surrogate Protein Stability

In this example, the efficacy of either sequential or concurrent treatment of prion surrogate protein (PSP) with ultrasonic energy and/or protease to destroy prions was evaluated.

PSP (available from BioResource International, Inc., Chapel Hill, N.C., catalog number PSP-001) was used to prepare ten samples for Western blot analysis. The samples were prepared as follows. Sonication was performed at approximately 8 watts continuously, with 9340 joules of energy. Unless otherwise indicated, the other conditions for sonication and protease digestions were as described in Example 2.

Sample 1: untreated PSP.

Sample 2: 50 µg PSP was sonicated for 20 minutes with no protease treatment.

Sample 3: 50 µg PSP was sonicated for 20 minutes, followed by digestion of the sonicated PSP with proteinase K (100:1 concentration PSP:proteinase K).

Sample 4: 50 µg PSP was sonicated for 20 minutes, with proteinase K added during sonication (100:1 concentration of PSP:proteinase K). Proteinase digestion was continued for 30 minutes.

Sample 5: 50 µg PSP was sonicated for 20 minutes, with proteinase K added during sonication (100:1 concentration of PSP:protease K). The proteinase K digestion was allowed to continue for an additional 30 minutes following sonication before the digestion was halted.

Sample 6: 50 µg PSP was sonicated for 20 minutes, with protease S (concentration unknown) added during sonication.

Sample 7: no PSP; sample comprised 7 µL of Bench Mark (Invitrogen, Carlsbad, Calif.) molecular weight marker.

Figure 3:
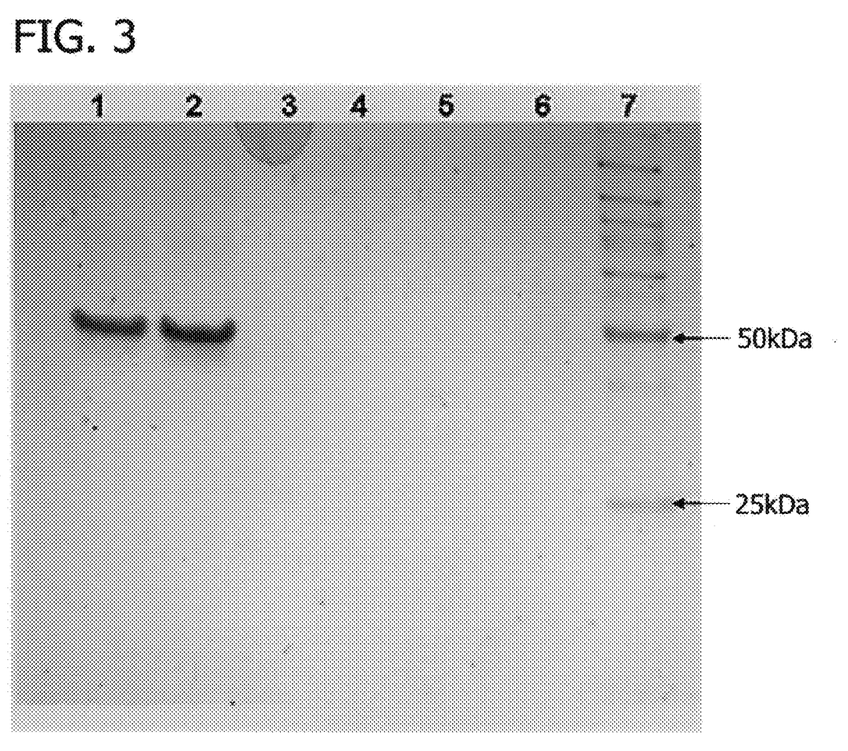
FIG. 3 is a Western blot of samples of PSP and/or proteinase K prepared under the conditions described in Example 3.

Samples were visualized using Western blotting, as described in Example 1. The results are shown in FIG. 3 and Table 1. In Table 1, a "+" indicates PSP was detected, and a "−" indicates PSP was not detected. The results for Samples 1-7 are shown as Lanes 1-7, respectively, in FIG. 3.

TABLE 1

| Sample | PSP detected? |
|---|---|
| 1 | + |
| 2 | + |
| 3 | − |
| 4 | − |
| 5 | − |
| 6 | − |
| 7 | n/a |

As can be seen from these results, no PSP was detected in samples treated concurrently with sonication and a protease (see Lanes 4, 5, and 6), or for samples treated sequentially with sonication followed by protease digestion (see Lane 3). These results indicate that both concurrent and sequential treatment of PSP with ultrasonic energy and protease may be effective to destroy prions.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. A method of disinfecting a surface contaminated with a prion protein or a surrogate thereof, the method comprising:
   treating the surface with a means for denaturing the prion protein, the denaturing means being selected from the group consisting of ultrasonic energy, electric fields, magnetic fields, and combinations thereof; and
   treating the surface with a degradation composition comprising one or more enzymes effective to cleave the prion protein into non-infective fragments;
   wherein the degradation composition is substantially free of a surfactant and comprises from about 3 to 5 percent weight of the protease and/or other proteolytic enzyme by weight of the degradation composition.

2. The method of claim 1 wherein the protease is proteinase K.

3. The method of claim 1 wherein the denaturing means is ultrasonic energy.

4. The method of claim 3 wherein the surface is treated with ultrasonic energy at a frequency of about 20 kHz to about 30 kHz.

5. The method of claim 1 wherein the surface is treated with the denaturing means for from about 0.5 minutes to about 120 minutes.

6. The method of claim 1 wherein the surface is treated with the degradation composition for from about 0.5 minutes to about 120 minutes.

7. The method of claim 1 wherein the surface is treated with the denaturing means prior to treating the surface with the degradation composition.

8. The method of claim 1 wherein the surface is simultaneously treated with the denaturing means and the degradation composition.

9. A method of disinfecting a surface contaminated with a prion protein or a surrogate thereof, the method comprising:
   treating the surface with a means for denaturing the prion protein, the denaturing means being selected from the group consisting of ultrasonic energy, electric fields, magnetic fields, and combinations thereof; and
   treating the surface with a degradation composition comprising one or more enzymes effective to cleave the prion protein into non-infective fragments;
   wherein the degradation composition has a pH of from about 6 to about 8 and comprises from about 3 to 5 percent weight of the protease and/or other proteolytic enzyme by weight of the degradation composition.

10. The method of claim 9 wherein the protease is proteinase K.

11. The method of claim 9 wherein the denaturing means is ultrasonic energy.

12. The method of claim 11 wherein the surface is treated with ultrasonic energy at a frequency of about 20 kHz to about 30 kHz.

13. The method of claim 9 wherein the surface is treated with the denaturing means for from about 0.5 minutes to about 120 minutes.

14. The method of claim 9 wherein the surface is treated with the degradation composition for from about 0.5 minutes to about 120 minutes.

15. The method of claim 9 wherein the surface is treated with the denaturing means prior to treating the surface with the degradation composition.

16. The method of claim 9 wherein the surface is simultaneously treated with the denaturing means and the degradation composition.

17. The method of claim 9 wherein the degradation composition further comprises at least one agent that promotes denaturation.

18. The method of claim 17 wherein the agent that promotes denaturation is selected from the group consisting of a surfactant, an organic solvent, an inorganic salt, a chaotropic agent, and combinations thereof.

19. The method of claim 18 wherein the surfactant is selected from the group consisting of anionic surfactants, cationic surfactants, non-ionic surfactants, zwitterionic surfactants, and combinations thereof.

20. The method of claim 9 wherein the method is performed at a temperature of from about 10° C. to about 95° C.

21. A method of disinfecting a surface, the method comprising:

treating the surface with a denaturing means selected from the group consisting of ultrasonic energy, electric fields, magnetic fields, and combinations thereof; and treating the surface with a degradation composition comprising one or more enzymes selected from the group consisting of proteases, proteolytic enzymes, and combinations thereof;

wherein the degradation composition has a pH of from about 6 to about 8 and comprises from about 3 to 5 percent weight of the protease and/or other proteolytic enzyme by weight of the degradation composition.

22. A method of disinfecting a surface, the method comprising:

treating the surface with a denaturing means selected from the group consisting of ultrasonic energy, electric fields, magnetic fields, and combinations thereof; and treating the surface with a degradation composition comprising one or more enzymes selected from the group consisting of proteases, proteolytic enzymes, and combinations thereof;

wherein the degradation composition is substantially free of a surfactant and comprises from about 3 to 5 percent weight of the protease and/or other proteolytic enzyme by weight of the degradation composition.

* * * * *